(12) United States Patent
Ravnikar et al.

(10) Patent No.: US 7,655,436 B1
(45) Date of Patent: Feb. 2, 2010

(54) EXPRESSION OF SOLUBLE HETEROLOGOUS PROTEINS IN BACTERIA UTILIZING A THIOREDOXIN/PROTEIN EXPRESSION VECTOR

(75) Inventors: Paula D. Ravnikar, Old Bridge, NJ (US); Robert Greenberg, Sparta, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 08/846,606

(22) Filed: Apr. 30, 1997

Related U.S. Application Data (60) Provisional application No. 60/011,606, filed on Apr. 30, 1996.

(51) Int. Cl.
  *C12N 15/09* (2006.01)
  *C12N 1/21* (2006.01)
  *C12N 15/70* (2006.01)

(52) U.S. Cl. .............. 435/69.1; 435/320.1; 435/252.3; 435/252.33

(58) Field of Classification Search ................ 435/69.1, 435/71.1, 320.1, 252.3, 252.33
See application file for complete search history.

(56) References Cited

FOREIGN PATENT DOCUMENTS

| | | |
|---|---|---|
| EP | 0 136 829 | 4/1985 |
| EP | 0 324 647 | 7/1989 |
| EP | 0 410 655 | 1/1991 |
| EP | 0 768 382 | 4/1997 |
| EP | 0 768 382 A2 * | 4/1997 |
| WO | WO 92/13955 | 8/1992 |
| WO | WO 94/02502 | 2/1994 |

OTHER PUBLICATIONS

LaVallie et al, 1993, *Bio/Technology* 11:187-193.
Yasukawa et al., 1995, *J. Biol. Chem.* 270(43):25328-25331.

* cited by examiner

*Primary Examiner*—Nancy Vogel (57) ABSTRACT

A method for producing a soluble, properly folded, biologically active protein in bacteria in which the heterologous protein is coexpressed with a thioredoxin protein.

13 Claims, 11 Drawing Sheets

Figure 1B

LIGATE
PCR FRAGMENT
AND
pMBD202020

DIGEST
pMBD112012
XbaI/BamHI

Figure 2C

LIGATE pDR75 and pMBD112012

Figure 3

IN THE CONSTRUCTION OF pDR109 THE trxA GENE WAS ALTERED TO REPLACE THE BSABI SITE WITH A UNIQUE XHOI RESTRICTION SITE FOR EASY SUBCLONING OF A DOWNSTREAM RECOMBINANT GENE.

EXPRESSION OF SOLUBLE HETEROLOGOUS PROTEINS IN BACTERIA UTILIZING A THIOREDOXIN/PROTEIN EXPRESSION VECTOR

This application claims the benefit of U.S. Provisional Application 60/011,606, filed Apr. 30, 1996.

BACKGROUND OF THE INVENTION

Expression of heterologous proteins in bacteria such as *E. coli* usually results in the formation of insoluble inclusion bodies that must be denatured and properly folded before the "natural" protein product is finally obtained. Thus there is a need to develop a bacterial expression system in which heterologous proteins can be expressed in the bacteria in a soluble, biologically active form.

SUMMARY OF THE INVENTION

The present invention fills this need by providing for a vector which coexpresses a heterologous protein and thioredoxin wherein the heterologous protein and the thioredoxin are expressed as separate, non-fused proteins.

DETAILED DESCRIPTION OF THE INVENTION

All references cited herein are incorporated herein by reference.

According to the process of the present invention heterologous proteins can be produced properly folded, soluble and biologically active by the coexpression of thioredoxin and the heterologous protein in bacteria especially *Escherichia coli* (*E. coli*). However, according to the present invention, the thioredoxin and the heterologous protein must be coexpressed as separate proteins and not as fused proteins.

As used herein, the term "transformed bacteria" means bacteria that have been genetically engineered to produce a mammalian protein. Such genetic engineering usually entails the introduction of an expression vector into a bacterium. The expression vector is capable of autonomous replication and protein expression relative to genes in the bacterial genome. Construction of bacterial expression is well known in the art, provided the nucleotide sequence encoding a desired protein is known or otherwise available. For example, DeBoer in U.S. Pat. No. 4,551,433 discloses promoters for use in bacterial expression vectors; Goeddel et al. in U.S. Pat. No. 4,601,980 and Riggs, in U.S. Pat. No. 4,431,739 disclose the production of mammalian proteins by *E. coli* expression systems; and Riggs supra, Ferretti et al. *Proc. Natl. Acad. Sci.* 83:599 (1986), Sproat et al., *Nucleic Acid Research* 13:2959 (1985) and Mullenbach et al., *J. Biol. Chem* 261:719 (1986) disclose how to construct synthetic genes for expression in bacteria.

Many bacterial expression vectors are available commercially and through the American Type Culture Collection (ATCC), Rockville, Md.

In the present invention a bacterium is transformed with vector containing a gene encoding a heterologous protein and a gene encoding a thioredoxin protein. An example of such a thioredoxin gene is SEQ ID NO:3. The following examples illustrate the coexpression of thioredoxin and heterologous proteins to produce properly folded proteins. The nucleic acid or gene which encodes the thioredoxin and the nucleic acid or gene which encodes the heterologous protein should be on the same vector such as a plasmid. Furthermore, it is even more preferable that the nucleic acid or gene which encodes the thioredoxin and the nucleic acid or gene which encodes the heterologous protein should be operationally linked to a common promoter such as the lac promoter.

Example 1

PCR Cloning of the Thioredoxin Gene from *E. coli*

*E. coli* chromosomal DNA was isolated from host strain MM294 according to the BioRad Instagene procedure. PCR primers were synthesized according to the published sequence for the thioredoxin (trxA) gene. The forward primer includes an NdeI site within the methionine start codon such that the trxA gene may be readily cloned and expressed by the cytoplasmic pMBD vectors illustrated in the figures shown below. The reverse primer includes a silent nucleotide change to generate a BsaBI site for future constructions and a BamHI site for expression vector cloning.

Forward Primer (SEQ ID NO:1)

```
                     NdeI
         CCTGTGGAGT TACATATGAG CGATAAAATT
```

Reverse Primer (SEQ ID NO:2)

```
                BamHI              BsaBI
GCACCCAACA TGCAAGGATC CTTACGCCAG ATTAGCATCG AGGAACT
```

This resulted in the following trxA gene (SEQ ID NO:3)

ATGAGCGATA AAATTATTCA CCTGACTGAC GACAGTTTTG ACACGGATGT ACTCAAAGCG GACGGGGCGA TCCTCGTCGA TTTCTGGGCA GAGTGGTGCG GTCCGTGCAA AATGATCGCC CCGATTCTGG ATGAAATCGC TGACGAATAT CAGGGCAAAC TGACCGTTGC AAAACTGAAC ATC- GATCAAA ACCCTGGCAC TGCGCCGAAA TATG- GCATCC GTGGTATCCC GACTCTGCTG CTGT- TCAAAA ACGGTGAAGT GGCGGCAACC AAAGTGGGTG CACTGTCTAA AGGTCAGTTG AAA- GAGTTCC TCGATGCTAA TCTGGCGTAA GGATCC

Figure 1A:
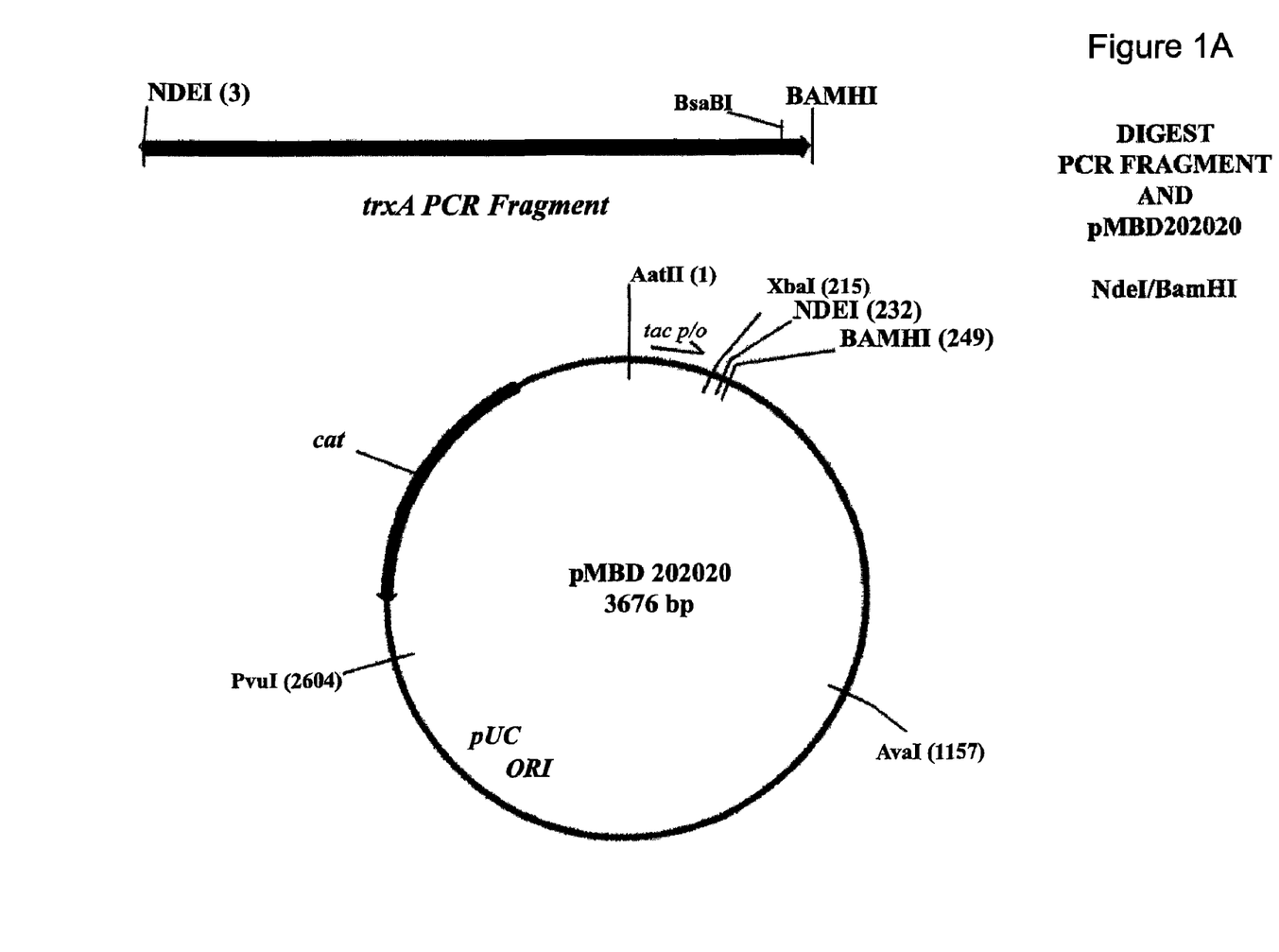
FIGS. 1A and 1B show schematically the construction of plasmid pDR75.
Figure 1B:
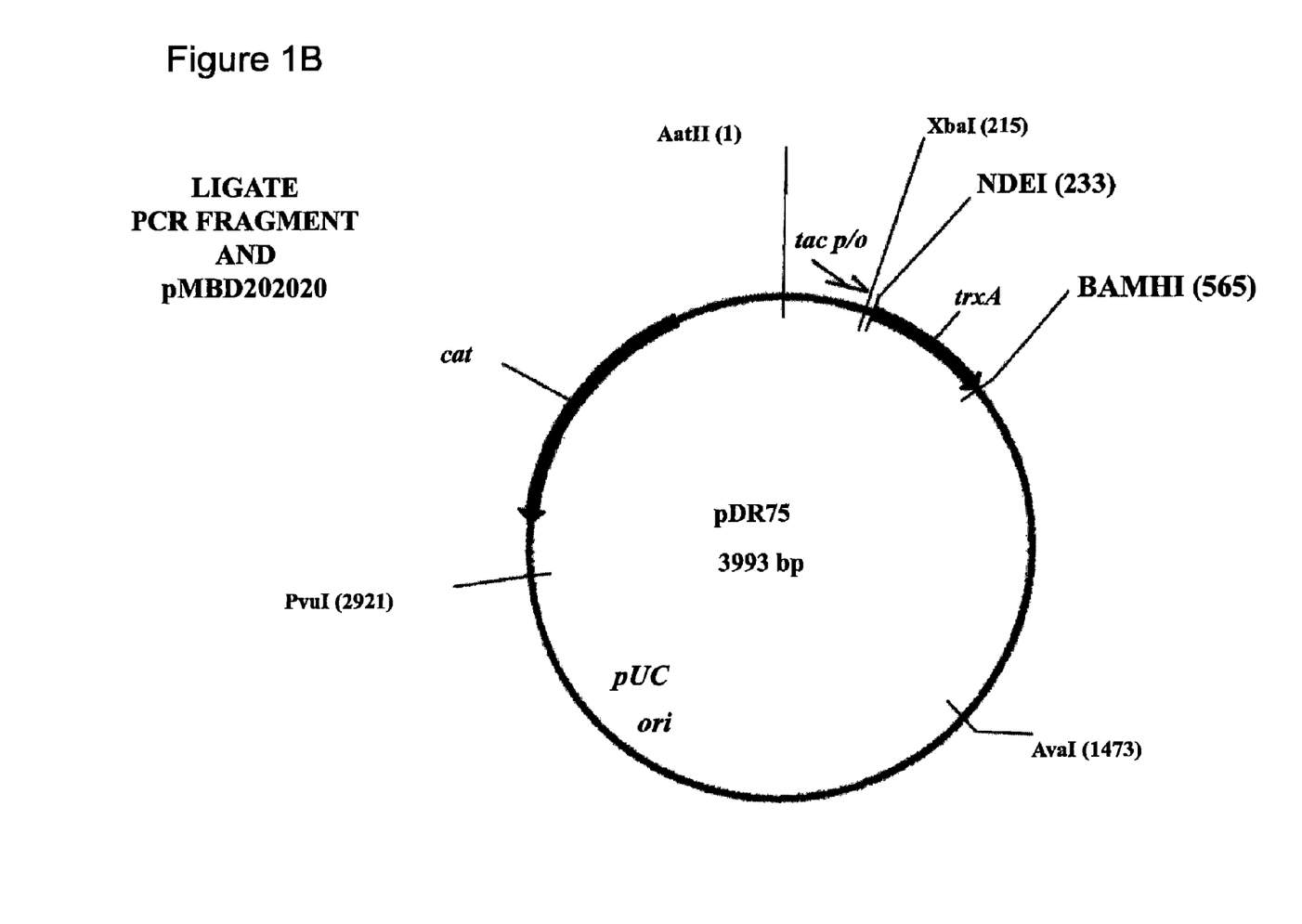

A PCR product of the anticipated size was obtained, NdeI/BamHI digested and cloned into NdeI/BamHI digested pMBD202020 as outlined in the figures. The insert DNA was verified to be correct by nucleotide sequence analysis and the clone was designated pDR75-11. (FIGS. 1A and 1B)

Example 2

Construction of a Regulated Vector Containing the trxA Vector

Figure 2A:
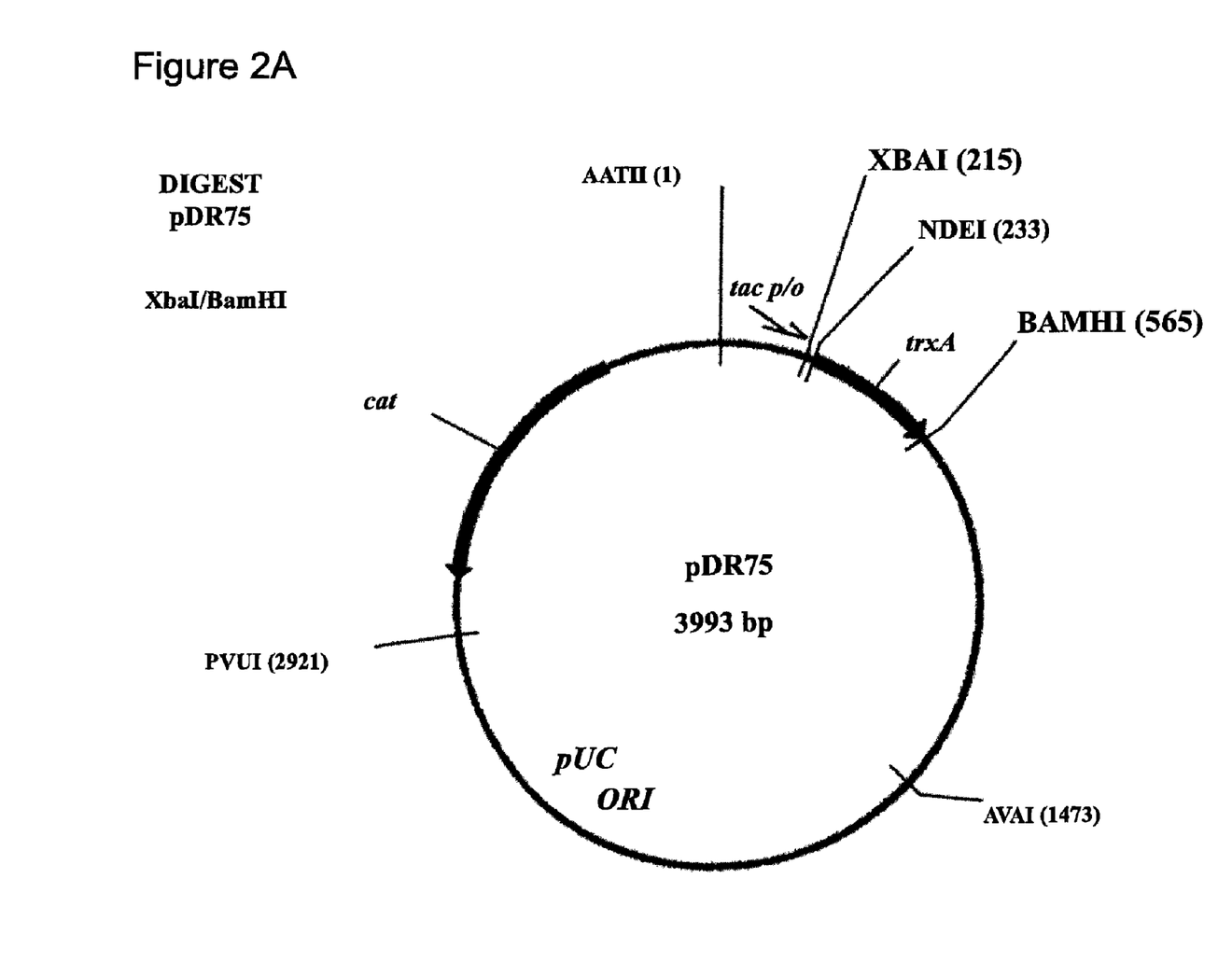
FIGS. 2A-2C show schematically the construction of plasmid pDR85.
Figure 2B:
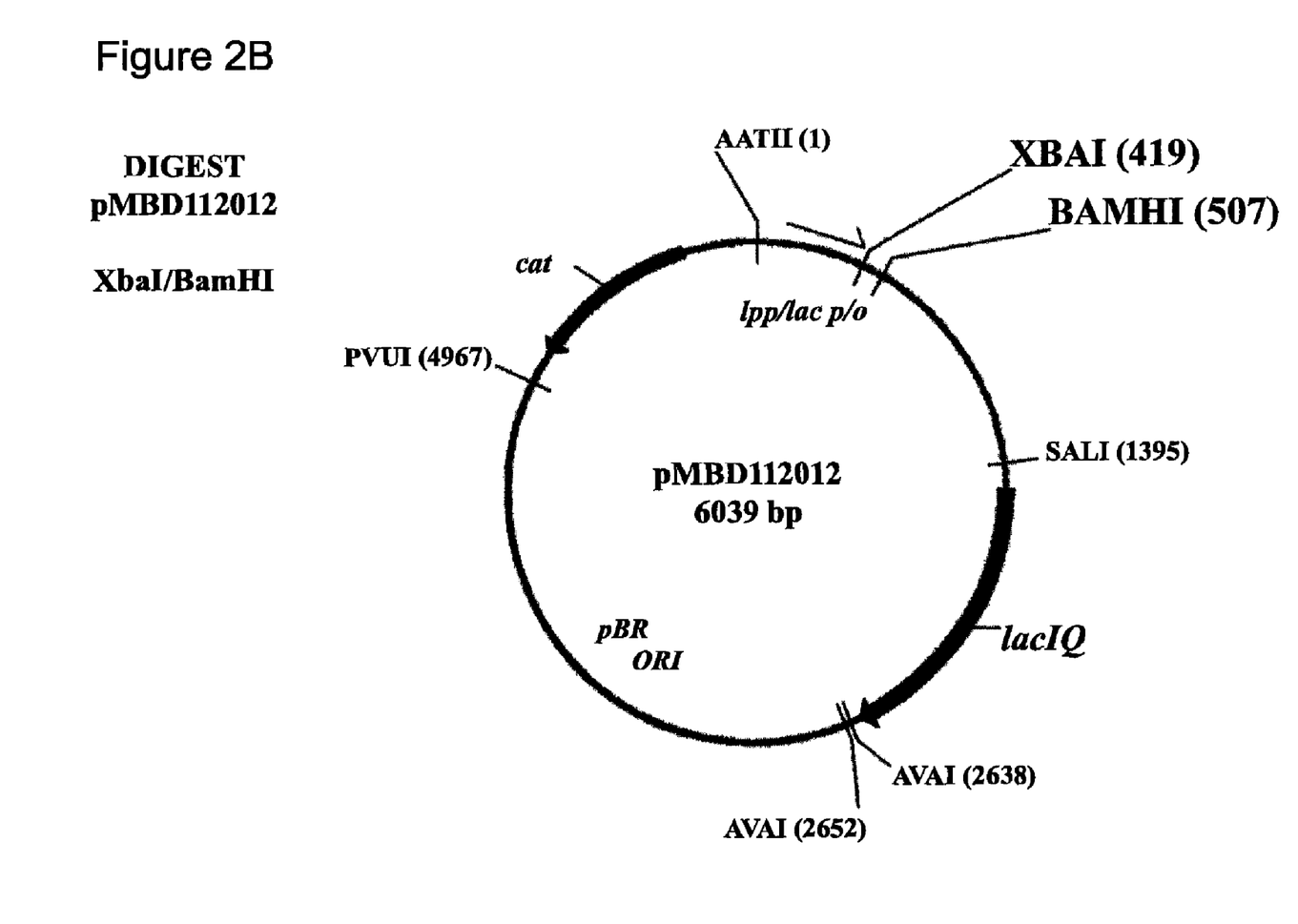
Figure 2C:
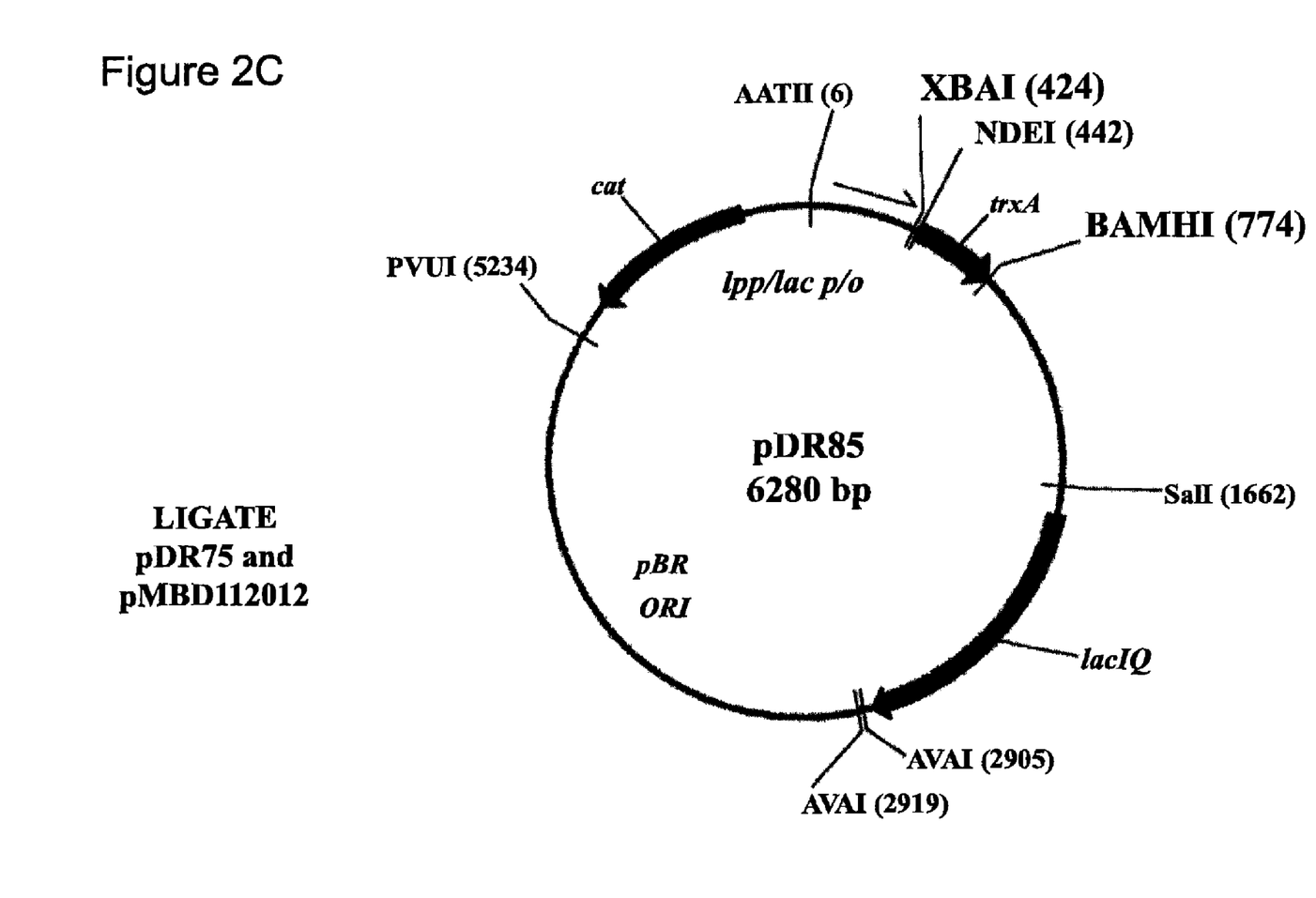

Vector pDR75-11 is a constitutive expression vector and it was desired to have a vector in which the expression of the trxA gene could be regulated. The trxA gene from pDR75-11 was subcloned as a XbaI/BamHI fragment into pMBD112012. The resulting plasmid was designated pDR85. The trxA gene is expressed from the Ipp/lac promoter-operator and is regulated by the lacIQ repressor. (FIGS. 2A-2C)

Example 3

Figure 3:
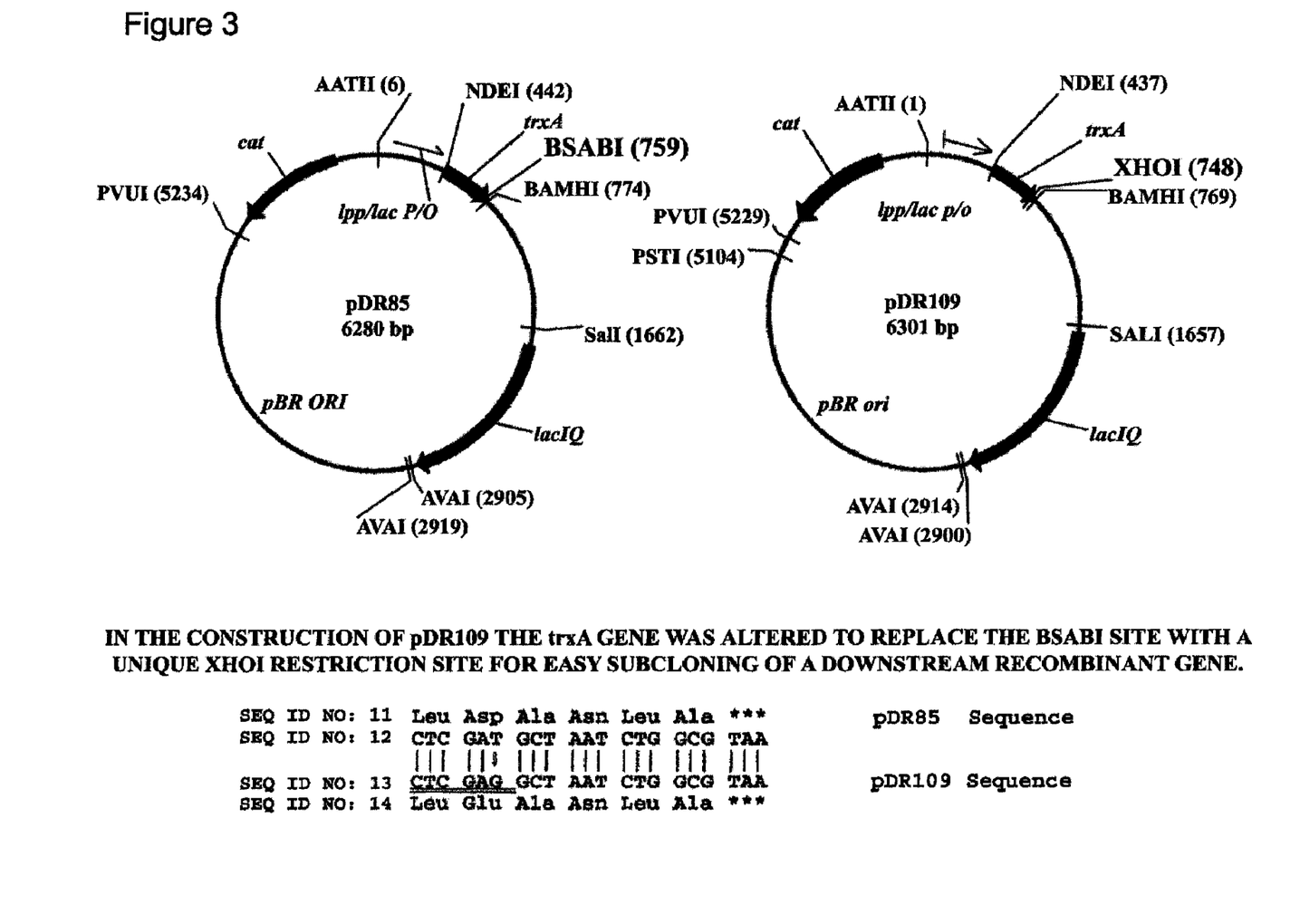
FIG. 3 shows schematically the construction of plasmid pDR109.

Plasmid pDR109 Construction (FIG. 3)

The trxA gene was altered to include a unique XhoI restriction site to allow for easy subcloning of a downstream recombinant protein. The trxA gene was PCR amplified.

A forward primer incorporated four nucleotide changes from the wild type *E. coli* DNA sequence so as to optimize the codon usage within the first five codons because optimal codon usage has been known to increase the efficiency of translation initiation. A reverse primer includes the incorporation of the XhoI site which results in a conservative amino acid change (aspartate to glutamate) in the thioredoxin protein.

The PCR product was subcloned into pMBD112012. The resulting plasmid expresses thioredoxin as a cytoplasmic protein from the lacIQ regulated lpp-lac promoter on a pBR322 replicon.

Shown below is the resultant trxA gene in pDR109 (SEQ ID NO:4)

| ATGAGCGATA | AAATTATTCA | CCTGACTGAC |
|---|---|---|
| GACAGTTTTG | ACACGGATGT | ACTCAAAGCG |
| GACGGGGCGA | TCCTCGTCGA | TTTCTGGGCA |
| GAGTGGTGCG | GTCCGTGCAA | AATGATCGCC |
| CCGATTCTGG | ATGAAATCGC | TGACGAATAT |

CAGGGCAAAC TGACCGTTGC AAAACTGAAC ATC-GATCAAA ACCCTGGCAC TGCGCCGAAA TATG-GCATCC GTGGTATCCC GACTCTGCTG CTGT-TCAAAA ACGGTGAAGT GGCGGCAACC AAAGTGGGTG CACTGTCTAA AGGTCAGTTG AAA-GAGTTCC TCGAGGCTAA TCTGGCGTAA GGATCC

Coexpression of thioredoxin and the recombinant protein is achieved by mimicking the translational coupling which occurs naturally in the tryptophan operon of *E. coli*. The ribosome binding site for the downstream gene is located within the 3' end of the preceding coding region and the stop and start codons of the adjacent genes are either overlapping or are immediately adjacent to each other.

The translationally coupled recombinant gene is generated by PCR amplification with a forward primer which includes the XhoI cloning site, sequences for the ribosomes binding site within the 3' end of the trxA gene, the stop codon for trxA (TAA) and the ATG start codon and the beginning DNA nucleotides of the recombinant gene. The incorporation of the ribosome binding site sequences within the 3' end of the trxA gene results in non-conservative amino acid changes within the protein.

Example 4

Construction of a trxA/Recombinant Human Interleukin-13

Figure 4A:
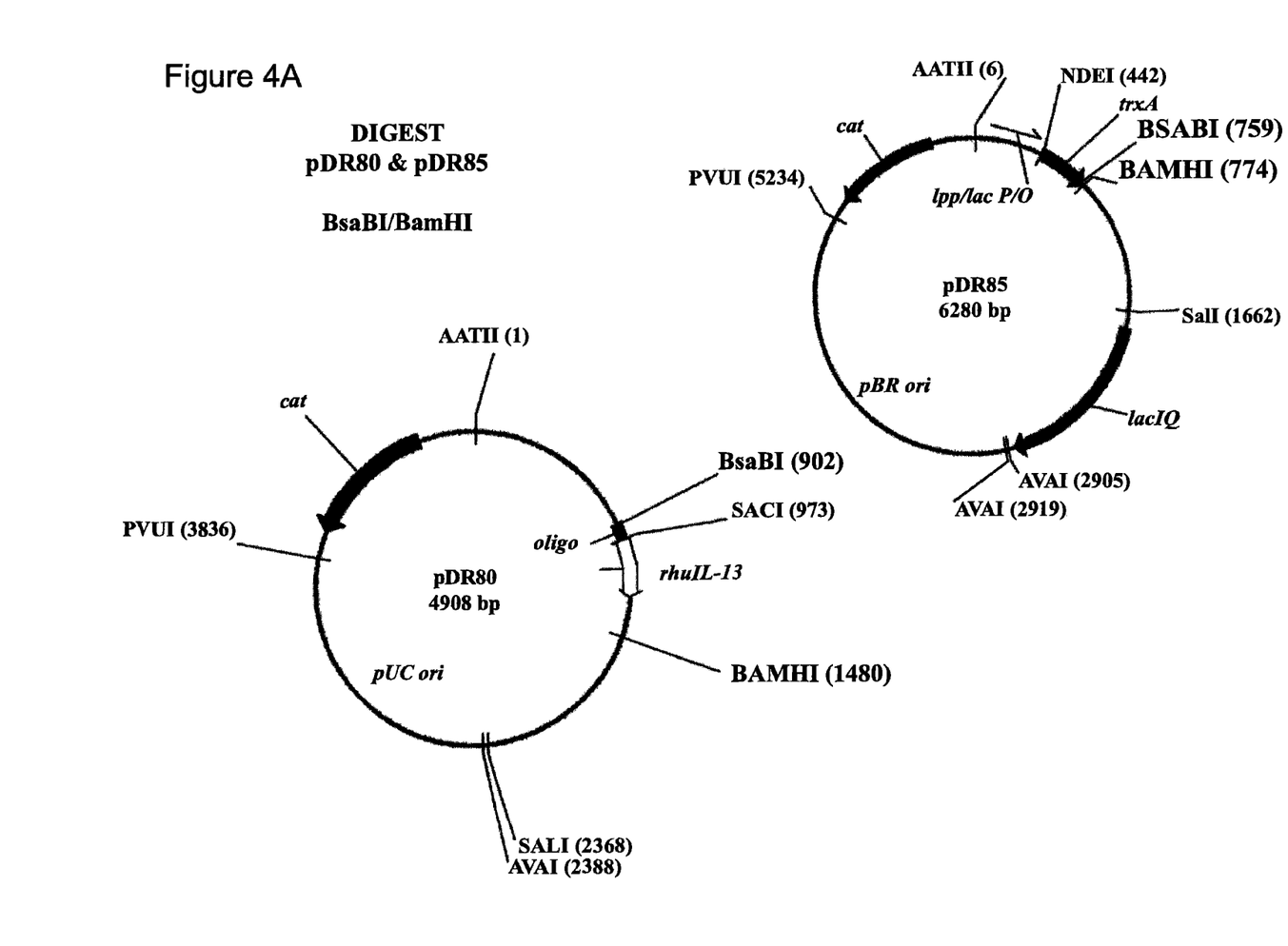
FIGS. 4A and 4B show schematically the construction of plasmid pDR88.
Figure 4B:
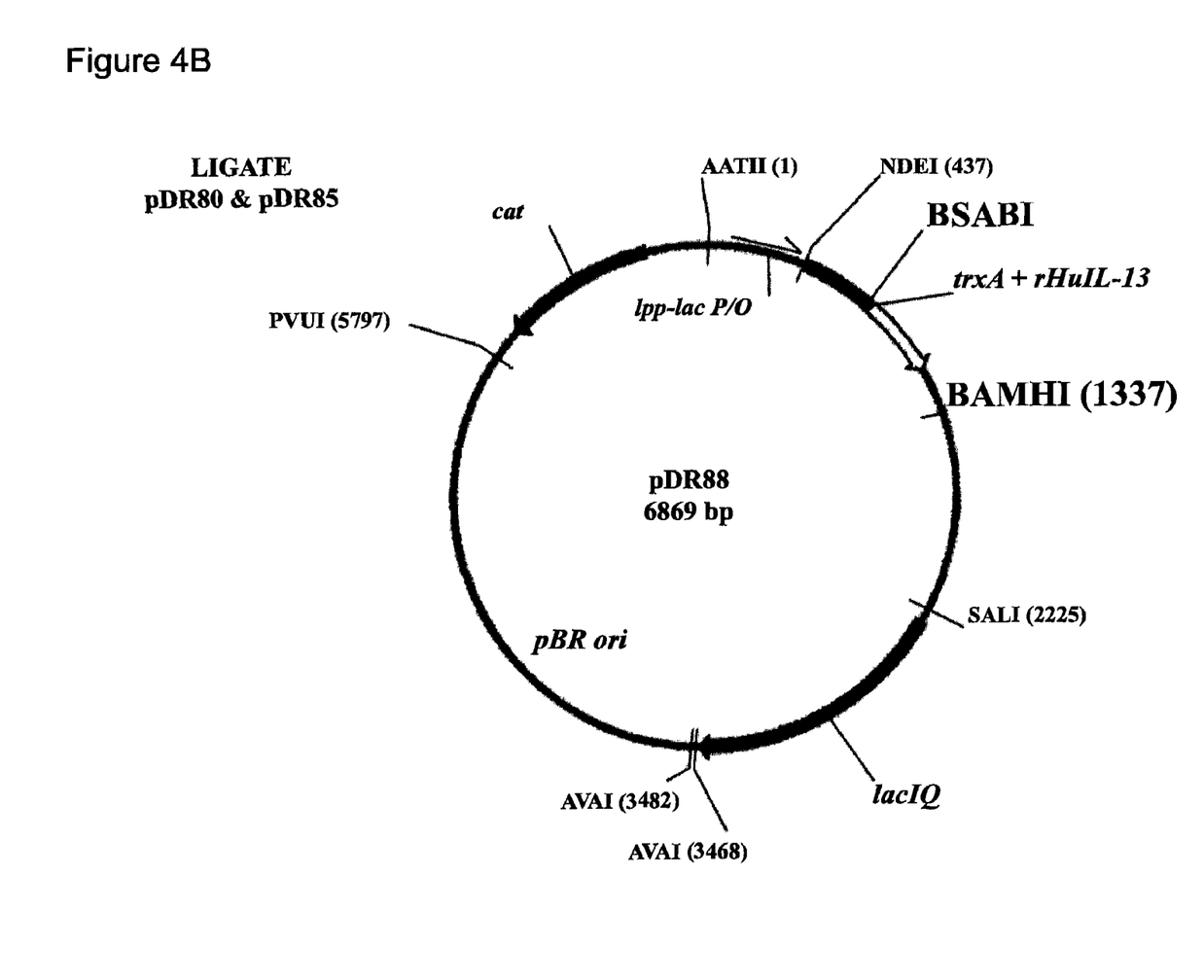

Vector pDR88 contains the trxA/recombinant human IL-13 (rhuIL-13) gene fusion with a gly/ser hinge linker+ enterokinase cleavage site as described by LaVallie, et al. (FIG. 4)

Figure 5:
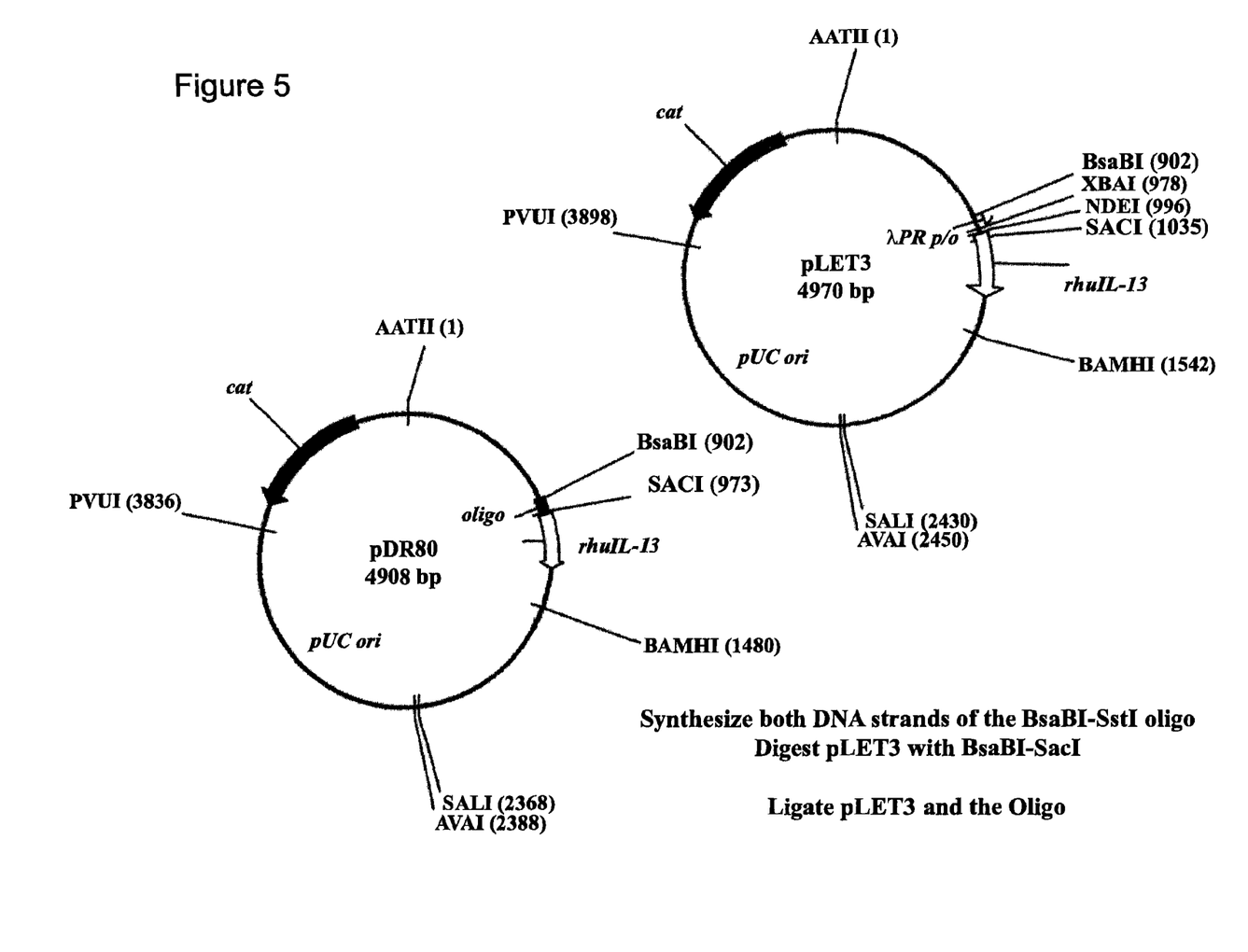
FIG. 5 shows schematically the construction of plasmid pDR80.

Linkers were attached to a rhuIL-13 clone (pLET3) which rated pDR80. The linkers contain the BsaBI site+gly/ser hinge linker+enterokinase cleavage site+rhu IL-13 codons+ SstI site (FIG. 5)

The BsaBI/BAMHI fragment from pDR80 was cloned into pDR85 to generate pDR88. (FIGS. 4A and 4B)

Sequence of the U411/U412 Linker Region (SEQ ID NO: 5 and SEQ ID NO: 6)

<u>BsaBI</u>

<u>GATAATAATCTG</u> GCT GGT TCT GGT TCT GGT GAT GAC GAT GAC AAG Asp Asn Asn Leu Ala Gly Ser Gly Ser Gly Asp Asp Asp Asp Lys ---trxA----------||Gly/Ser hinge ----||enterokinase cleavage <u>SstI</u>

GGT CCT GTT CCG CCG TCT ACC GCT CTG CGT <u>GAGCTC</u> Gly Pro Val Pro Pro Ser Thr Ala Leu Arg Glu Leu

Example 5 trx Gene Translationally Coupled to the rhuIL-13 Gene

Figure 6:
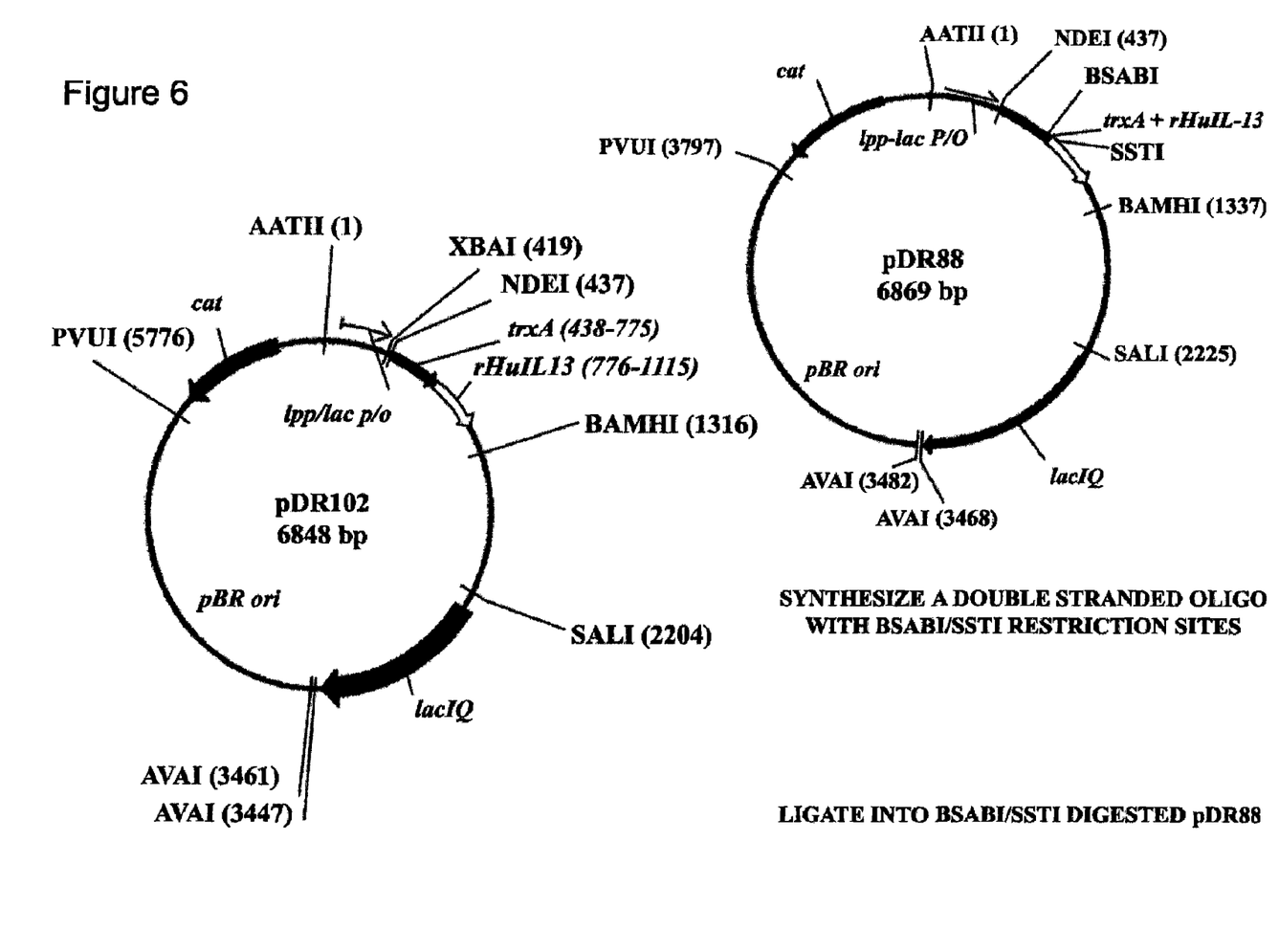
FIG. 6 shows schematically the construction of plasmid pDR102.

A BsaBI/Sst linker was synthesized to include a ribosome binding site and coupled stop/start codon for trxA/rhu IL-13. The double stranded oligo was cloned into pDR88 to generate pDR102. (FIG. 6)

Translational Coupling Sequence in pDR102 (SEQ ID NO:7)

```
     R.B.S.         IL-13                            SstI
     GAAGGAGGCT GATTAAATGGGTCCGGTTCCGCCGTCTACCGCTCTGGAGCTC
```

Recombinant Human IL-13 (rhu IL-13) was translationally coupled to thioredoxin with the following sequence: (SEQ ID NO:8)

```
        RBS    |----8bp--- |
    ----AAG GAG GCT GAT TAA ATG----------
    --trxA----------------|Met ---rhuIL-13
```

The resultant plasmid (designated pDR102) (FIG. 6) was transformed into *E. coli* host strain MM294 and fermentation analysis was done to confirm protein expression. The culture was induced for expression and grown at 15° C. to maximize the accumulation of rhuIL-13 soluble protein. Cells were harvested at 48 and 68 hrs post induction. Accumulation of soluble protein immunoreactive to anti-IL-13 antibody and of monomeric (non-fused) size was observed at both times.

Example 6

Fermentation Analysis of rhu IL-10 and rhuIL-13 Production from trxA Plasmids Alternative coupling sequences were analyzed for rhuIL-13 clones. The two alternative sequences in pDR113 and pDR114 differ from pDR102 in that the stop codon (TAA) for trxA and the start codon (ATG) for rhIL-13 overlap each other as the TAATG sequence. In addition, the spacing between the ribosome binding site (RBS) and the ATG start codon is shorter, reduced to 7 bp in pDR113 and to 4 bp in pDR114.

```
       RBS   | --7bp-- |
----AAG GAG GCT GAT TAATG----  (SEQ ID NO:9) pDR113
--trxA-----------     |Met--rhuIL-13

RBS    |-4 bp-|
------ AAG GAG GTT TAATG---
------trxA-----------  |Met---rhu IL-13 (SEQ ID NO:10) pDR114
```

Fermentations were done at 15° C. Soluble protein is produced in pDR113 and pDR114.

Attempts were made to enhance protein expression from pDR102 by using the Tac promoter instead of the lpp-lac promoter and by increasing plasmid copy number by utilizing the pUC origin of replication.

Figure 7:
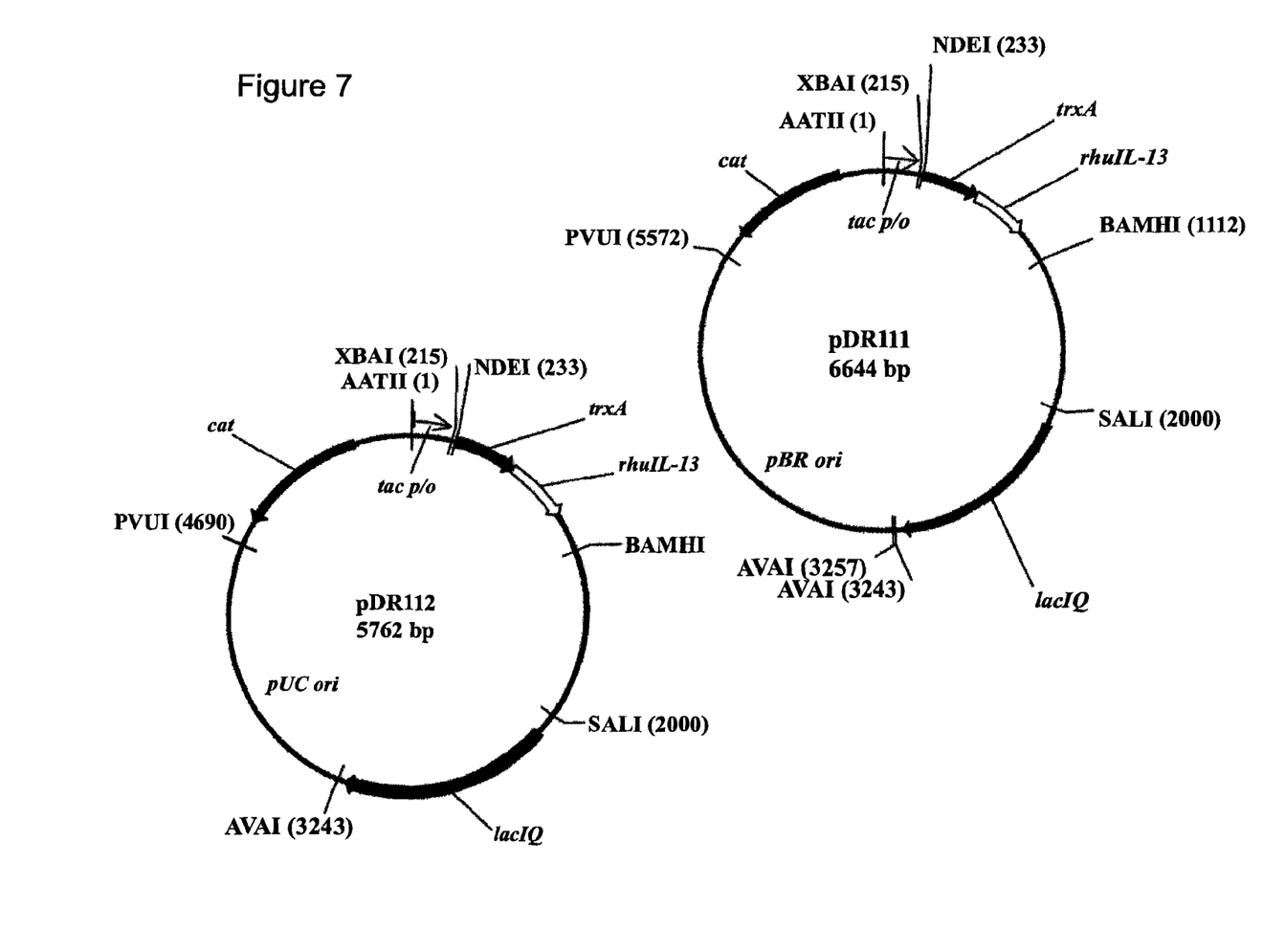
FIG. 7 shows schematically the construction of plasmid pDR112.

Plasmid pDR111 contains the pDR102 coupling expressed from the Tac promoter. Plasmid pDR112 utilizes the pDR102 coupling expressed from the Tac promoter and pUC origin of replication. (FIG. 7)

Fermentations were done at 15° C. Soluble protein was produced in both pDR111 and pDR112.

Example 7

Coexpression of Thioredoxin and Recombinant Human Interleukin-10

A trxA/rhuIL-10 fusion plasmid was made and designated pDR130. Fermentations were performed at 15° C., 25° C. and 37° C. Production of soluble trxA-rhuIL-10 fusion protein was greatest at 15° C. and still detectable at 37° C. Protein material remained in the soluble fraction after 90 minutes centrifugation at 40,000 rpm.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method for expressing a soluble heterologous protein in bacteria comprising: transforming a bacterium with a vector wherein the vector contains a nucleic acid sequence which expresses thioredoxin and a nucleic acid sequence which expresses a heterologous protein; and culturing the bacterium under conditions wherein the thioredoxin and the heterologous protein are expressed as separate non-fused proteins and the heterologous protein is expressed in a soluble, biologically active form.

2. The method of claim 1 wherein the vector is a plasmid.

3. The method of claim 1 wherein the nucleic acid sequence which expresses thioredoxin and the nucleic acid sequence which expresses the heterologous protein are operationally linked to a common promoter.

4. The method of claim 3 wherein the promoter is a lac promoter.

5. A vector which contains a nucleic acid sequence which encodes a thioredoxin protein and a nucleic acid sequence which encodes a heterologous protein wherein the vector expresses the thioredoxin protein and the heterologous protein as separate, nonfused proteins, and wherein the heterologous protein is expressed in a soluble, biologically active form.

6. The vector of claim 5 wherein the vector is a plasmid.

7. The vector of claim 5 wherein the nucleic acid sequence which encodes the thioredoxin protein and the nucleic acid sequence which encodes the heterologous protein are operationally linked to a common promoter.

8. The vector of claim 7 wherein the promoter is a lac promoter.

9. A bacterium transformed with an expression vector containing a nucleic acid encoding a thioredoxin protein and a nucleic acid encoding a heterologous protein wherein the thioredoxin protein and the heterologous protein are expressed as separate proteins and wherein the heterologous protein is expressed in a soluble, biologically active form.

10. The bacterium of claim 9 wherein the bacterium is *Escherichia coli*.

11. The bacterium of claim 9 wherein the vector is a plasmid.

12. The bacterium of claim 9 wherein the nucleic acid which encodes the thioredoxin and the nucleic acid which encodes the heterologous protein are operationally linked to a common promoter.

13. The bacterium of claim 12 wherein the promoter is a lac promoter.

* * * * *

SEQUENCE LISTING

```
(1) GENERAL INFORMATION:

(iii) NUMBER OF SEQUENCES: 14

(2) INFORMATION FOR SEQ ID NO:1:

(i) SEQUENCE CHARACTERISTICS:
        (A) LENGTH: 30 bases
        (B) TYPE: nucleic acid
        (C) STRANDEDNESS: single
        (D) TOPOLOGY: linear (ii) MOLECULE TYPE: DNA (xi) SEQUENCE DESCRIPTION:  SEQ ID NO:1:

CCTGTGGAGT TACATATGAG CGATAAAATT                                          30

(2) INFORMATION FOR SEQ ID NO:2:

(i) SEQUENCE CHARACTERISTICS:
        (A) LENGTH: 47 bases
        (B) TYPE: nucleic acid
        (C) STRANDEDNESS: single
        (D) TOPOLOGY: linear (ii) MOLECULE TYPE: DNA (xi) SEQUENCE DESCRIPTION:  SEQ ID NO:2:

GCACCCAACA TGCAAGGATC CTTACGCCAG ATTAGCATCG AGGAACT                       47

(2) INFORMATION FOR SEQ ID NO:3:

(i) SEQUENCE CHARACTERISTICS:
        (A) LENGTH: 336 base pairs
        (B) TYPE: nucleic acid
```

(C) STRANDEDNESS: single
            (D) TOPOLOGY: linear (ii) MOLECULE TYPE: DNA (xi) SEQUENCE DESCRIPTION: SEQ ID NO:3:

```
ATGAGCGATA AAATTATTCA CCTGACTGAC GACAGTTTTG ACACGGATGT          50

ACTCAAAGCG GACGGGGCGA TCCTCGTCGA TTTCTGGGCA GAGTGGTGCG          100

GTCCGTGCAA AATGATCGCC CCGATTCTGG ATGAAATCGC TGACGAATAT         150

CAGGGCAAAC TGACCGTTGC AAAACTGAAC ATCGATCAAA ACCCTGGCAC         200

TGCGCCGAAA TATGGCATCC GTGGTATCCC GACTCTGCTG CTGTTCAAAA         250

ACGGTGAAGT GGCGGCAACC AAAGTGGGTG CACTGTCTAA AGGTCAGTTG         300

AAAGAGTTCC TCGATGCTAA TCTGGCGTAA GGATCC                        336
```

(2) INFORMATION FOR SEQ ID NO:4:

(i) SEQUENCE CHARACTERISTICS:
        (A) LENGTH: 336 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
ATGAGCGATA AAATTATTCA CCTGACTGAC GACAGTTTTG ACACGGATGT          50

ACTCAAAGCG GACGGGGCGA TCCTCGTCGA TTTCTGGGCA GAGTGGTGCG         100

GTCCGTGCAA AATGATCGCC CCGATTCTGG ATGAAATCGC TGACGAATAT         150

CAGGGCAAAC TGACCGTTGC AAAACTGAAC ATCGATCAAA ACCCTGGCAC         200

TGCGCCGAAA TATGGCATCC GTGGTATCCC GACTCTGCTG CTGTTCAAAA         250

ACGGTGAAGT GGCGGCAACC AAAGTGGGTG CACTGTCTAA AGGTCAGTTG         300

AAAGAGTTCC TCGAGGCTAA TCTGGCGTAA GGATCC                        336
```

(2) INFORMATION FOR SEQ ID NO:5:

(i) SEQUENCE CHARACTERISTICS:
        (A) LENGTH: 81 bases pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
GATAATATTC TGGCTGGTTC TGGTTCTGGT GATGACGATG ACAAGGGTCC          50

TGTTCCGCCG TCTACCGCTC TGCGTGAGCT C                              81
```

(2) INFORMATION FOR SEQ ID NO:6:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO:6:

```
Asp Asn Asn Leu Ala Gly Ser Gly Ser Gly Asp Asp Asp Lys
 1               5                  10                  15
```

Gly Pro Val Pro Pro Ser Thr Ala Leu Arg Glu Leu
                20                  25

(2) INFORMATION FOR SEQ ID NO:7:

(i) SEQUENCE CHARACTERISTICS:
        (A) LENGTH: 52 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

GAAGGAGGCT GATTAAATGG GTCCGGTTCC GCCGTCTACC GCTCTGGAGC         50

TC                                                            52

(2) INFORMATION FOR SEQ ID NO:8:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

AAGGAGGCTG ATTAAATG                                           18

(2) INFORMATION FOR SEQ ID NO:9:

(i) SEQUENCE CHARACTERISTICS:
        (A) LENGTH: 17 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

AAGGAGGCTG ATTAATG                                            17

(2) INFORMATION FOR SEQ ID NO:10:

(i) SEQUENCE CHARACTERISTICS:
        (A) LENGTH: 14 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

AAGGAGGTTT AATG                                               14

(2) INFORMATION FOR SEQ ID NO:11:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:11:

Leu Asp Ala Asn Leu Ala

-continued

```
          1           5

(2) INFORMATION FOR SEQ ID NO:12:

(i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: DNA (xi) SEQUENCE DESCRIPTION:  SEQ ID NO:12:

CTCGATGCTA ATCTGGCGTA A                                                 21

(2) INFORMATION FOR SEQ ID NO:13:

(i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: DNA (xi) SEQUENCE DESCRIPTION:  SEQ ID NO:13:

CTCGAGGCTA ATCTGGCGTA A                                                 21

(2) INFORMATION FOR SEQ ID NO:14:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION:  SEQ ID NO:14:

Leu Glu Ala Asn Leu Ala
  1               5
```